(12) United States Patent
Foley et al.

(10) Patent No.: US 9,474,538 B2
(45) Date of Patent: Oct. 25, 2016

(54) SYSTEMS AND METHODS FOR GUIDING ANCHORS FOR FACET FIXATION

(75) Inventors: Kevin T. Foley, Germantown, TN (US); Gregory C. Marik, Collierville, TN (US); Newton H. Metcalf, Jr., Memphis, TN (US); Danish Siddiqui, Northbrook, IL (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 373 days.

(21) Appl. No.: 13/552,378

(22) Filed: Jul. 18, 2012

(65) Prior Publication Data

US 2014/0025121 A1  Jan. 23, 2014

(51) Int. Cl.
*A61B 17/90* (2006.01)
*A61B 17/17* (2006.01)
*A61B 17/34* (2006.01)
*A61B 17/88* (2006.01)

(52) U.S. Cl.
CPC ....... *A61B 17/1757* (2013.01); *A61B 17/3421* (2013.01); *A61B 17/8886* (2013.01)

(58) Field of Classification Search
CPC .......... A61B 17/7064; A61B 17/1757; A61B 17/7085
USPC ............................ 606/96, 104, 54–59, 324
See application file for complete search history.

(56) References Cited

U.S. PATENT DOCUMENTS

| | | | |
|---|---|---|---|
| 2,398,915 A * | 4/1946 | Bell ................. | A61B 17/685 |
| | | | 279/44 |
| 4,872,451 A * | 10/1989 | Moore et al. ................ | 606/916 |
| 5,242,444 A * | 9/1993 | MacMillan ................ | 606/86 R |
| 5,334,205 A * | 8/1994 | Cain ................. | 606/96 |
| 6,342,056 B1 * | 1/2002 | Mac-Thiong et al. .......... | 606/96 |
| 8,317,862 B2 * | 11/2012 | Troger et al. ............. | 623/13.11 |
| 8,361,079 B2 * | 1/2013 | Pandya ........................ | 606/96 |
| 2008/0188852 A1 * | 8/2008 | Matityahu .......... | A61B 17/1728 |
| | | | 606/54 |
| 2010/0121338 A1 * | 5/2010 | Pandya ....................... | 606/96 |
| 2010/0121447 A1 * | 5/2010 | Troger et al. ............ | 623/13.11 |
| 2010/0179550 A1 * | 7/2010 | Schreiber et al. ............ | 606/62 |
| 2011/0009869 A1 * | 1/2011 | Marino et al. ................ | 606/87 |
| 2011/0238181 A1 * | 9/2011 | Trieu ................. | A61B 17/7055 |
| | | | 623/17.11 |

FOREIGN PATENT DOCUMENTS

GB  2230453 A * 10/1990 ......... A61B 17/1714

* cited by examiner

*Primary Examiner* — Jan Christopher Merene (57) ABSTRACT

Apparatus and methods for spinal surgery include a retractor with an elongated body extending along a longitudinal axis between a distal end and an opposite proximal end. The retractor defines a passage between the distal and proximal ends and a window opening into the passage adjacent to the distal end. The apparatus also includes a guide member extending laterally from the proximal end of the retractor and the guide member includes a body extending along an arc. The body defines a number of trajectories each intersecting the window of the retractor. The apparatus further includes an instrument removably mounted to the guide member and the instrument is movable along the guide member and securable to the guide member in any one of the number of trajectories so that the instrument can be moved along the selected trajectory through the window.

20 Claims, 3 Drawing Sheets

SYSTEMS AND METHODS FOR GUIDING ANCHORS FOR FACET FIXATION

FIELD OF THE INVENTION

The invention relates generally to medical devices and procedures. More particularly, the invention relates to apparatus and methods for minimally invasive instrumentation, implants and methods for spinal surgery.

BACKGROUND

Bone fixation devices, such as, for example, bone screws, interbody implants, staples, pins, wires and/or clamping mechanisms, can be used in various medical procedures. For example, known bone screws can be used to repair fractured bone tissue by securing adjacent portions of the bone tissue together to stabilize and/or limit the movement of bone tissue. Known interbody implants can be used between adjacent portions of bone tissue to provide support for and to facilitate bone growth between the portions of bone tissue. For example, some known bone screws and interbody implants can be used as a part of a spinal fixation procedure.

In some procedures, for example, a facet screw can be inserted across the facet joint of the spinal column to fix and/or limit the motion of the facet joint. Such known procedures can include, for example, translaminar facet screw fixation, which includes inserting a facet screw from the base of the spinous process on the contralateral side and through the lamina to traverse the facet joint in a plane perpendicular to the joint surfaces. Facet screws can also be inserted using a transfacet approach, which involves inserting a bone screw via a midline incision or an ipsilateral incision. Such known procedures, however, often involve the use of multiple tools and/or multiple steps, and are performed in an open incision in which the facet joint is exposed and tissue retracted sufficiently to allow placement of the screw through the facet.

Thus, a need exists for improved insertion tools, implants, and procedures for insertion and securement of implants at locations within a patient's body that can minimize intrusion into tissue along the approach to and around the implantation location.

SUMMARY

Apparatus and methods for spinal surgery are described herein. The apparatus and methods can be employed in minimally invasive surgical techniques for placement of a bone anchor across, for example, a facet joint. Applications in non-minimally invasive procedures and in other locations are also contemplated.

According to one aspect, the apparatus includes a retractor including an elongated body extending along a longitudinal axis between a distal end and an opposite proximal end. The retractor defines a passage between the distal and proximal ends and a window opening into the passage adjacent to the distal end. The apparatus also includes a guide member extending laterally from the proximal end of the retractor and the guide member includes a body extending along an arc. The body defines a number of trajectories each intersecting the window of the retractor. The apparatus further includes an instrument removably mounted to the guide member and the instrument is movable along the guide member and securable to the guide member in any one of the number of trajectories so that the instrument can be moved along the selected trajectory through the window.

According to a further aspect, an apparatus includes a retractor including an elongated tubular body extending along a longitudinal axis between a distal end and an opposite proximal end. The retractor defines a working channel between the distal and proximal ends and a window extending proximally from the distal end of the tubular body that opens through the body into the working channel. The retractor is configured for positioning in a body of a patient with the distal end adjacent an implantation location in the body of the patient while the proximal end is located outside the body of the patient. The apparatus also includes a guide member extending laterally from the proximal end of the retractor. The guide member includes an elongated body defining a number of trajectories that each intersect the window of the retractor. A driver instrument is removably mounted to the guide member and is movable along the guide member and securable to the guide member in any selected one of the number of trajectories so that the driver instrument can be moved along the selected trajectory through the window. A bone anchor is removably engaged to a distal end of the driver instrument and the bone anchor is positionable through the window along the selected trajectory for implantation into bony structure under direct vision through the working channel of the retractor.

According to yet another aspect, a method comprises: inserting through a first opening in a patient a distal end portion of a retractor that defines a passage extending between a distal end and a proximal end of the retractor, wherein the retractor defines a window through the retractor that opens into the passage adjacent the distal end of the retractor; inserting into the patient an instrument that is guided along a selected trajectory that is defined by a guide member extending laterally from the proximal end of the retractor, the guide member defining a plurality of trajectories that extend through the window, and the selected trajectory is selected from the plurality of trajectories; and securing an anchor to bony structure in the patient through the window along the selected trajectory under direct vision through the passage of the retractor.

These and other aspects are also discussed below.

DETAILED DESCRIPTION

For the purposes of promoting an understanding of the principles of the invention, reference will now be made to the embodiments illustrated in the drawings and specific language will be used to describe the same. It will nevertheless be understood that no limitation on the scope of the invention is intended. Any alterations and further modifications in the illustrated devices and described methods and further applications of the principles of the invention as disclosed herein are contemplated as would normally occur to one skilled in the art to which the invention relates.

Apparatus and methods for inserting bone anchors to bony portions of the spinal column are described herein. In one embodiment, the apparatus includes a retractor with an elongated body defining a passage extending between a distal end and a proximal end. The retractor includes a window extending proximally from the distal end. The proximal end of the retractor includes a guide member extending laterally therefrom. The guide member is engaged to an instrument. The guide member orients the instrument so that it intersects the window of the retractor. The instrument is movable relative to the guide member to, for example, engage the anchor to a bony element of the spinal column under direct vision through the channel of the retractor. The instrument is also moveable along the guide member to change the trajectory of the instrument relative to the retractor while maintaining the insertion instrument in an orientation that intersects the window. In one embodiment, the anchor is a bone screw and the instrument is a screwdriver that is used to engage the bone screw to a facet joint of adjacent vertebrae.

A method includes inserting percutaneously or through a small incision a distal end portion of a retractor that includes a window and guiding an instrument through the window with a guide member extending laterally from the proximal end of the retractor. The guide member is arranged to orient the instrument in intersecting relation with the window. The instrument can also be movable along the guide member to change the trajectory of the instrument relative to the retractor into the patient while maintaining the instrument in intersection relation to the window. Placement of the instrument and/or anchor through the window can be directly visualized through a passage defined by the retractor. In one embodiment, the guide member guides a forming instrument through the window. The forming instrument can be any instrument that forms an implantation location for an anchor, such as a drill, tap, reamer, guidewire, or dilator, for example. In another embodiment, the instrument is a screwdriver that is secured to the anchor and used to drive the anchor into bone of the patient. The screwdriver can be configured to retain anchor in the end thereof so that the screwdriver can be inserted into the patient to the implantation location with the screwdriver. In one specific embodiment, the guide member is arranged to guide instruments and/or anchors along an approach to a facet joint that is substantially oblique to the approach along which the retractor is positioned to the facet joint.

In some embodiments, a kit includes a retractor with a guide member, an instrument that is movable along the guide member while maintaining an intersecting relationship with a window of the retractor, and a bone anchor that is insertable through the window and into a bony portion of the patient with the instrument guided by the guide member. The trajectory of the instrument into the patient can be adjusted by moving the instrument along the guide member. In one specific embodiment, the guide member includes a clamping mechanism that secures the instrument in position along the guide member while allowing the instrument to move along the selected trajectory and through the window of the retractor.

Referring to FIGS. 1-4, there is shown an apparatus 10 that includes a retractor 12 that defines a passage extending along a longitudinal axis 14 between a distal end 16 and a proximal end 18. Apparatus 10 also includes a guide member 40 extending laterally from or adjacent to proximal end 18 of retractor 12. Guide member 40 includes an elongated body portion 42 extending between an inner end portion 44 adjacent to retractor 12 and an opposite outer end 46. Body 42 also includes a distal side 48 and an opposite proximal side 50 extending between ends 44, 46. A slot 52 extending along body 42 and opens through distal and proximal sides 48, 50. An instrument 80 is positioned in slot 52 and movable along guide member 40 to adjust the trajectory of instrument 80 into the patient and relative to retractor 12.

Guide member 40 is configured so that instrument 80 and/or its trajectory maintain a fixed or substantially fixed intersection location with retractor 12 as instrument 80 is moved along guide member 40 to adjust its trajectory. In the illustrated embodiment, body portion 42 and slot 52 are curved along an arc A that is defined by a radius. The curved configuration of guide member portion 42 and slot 52 along arc A allows the trajectory of instrument 80 into the patient to be varied by moving instrument 80 along slot 52 as indicated by arrow 43 in FIG. 1, while maintaining the intersecting relation of instrument 80 with retractor 12.

Inner end portion 44 of guide member 40 is mounted to proximal end 18 of retractor 12. In the illustrated embodiment, inner end portion 44 includes a mounting member 54 secured to the proximal end of retractor 12, a first arm portion 56 extending laterally from and aligned generally with proximal end 18, and a second arm portion 58 extending proximally and obliquely away from retractor 12 and first arm portion 56 to body portion 42. Inner end portion 44 thus positions body portion 42 in a proximally offset and laterally offset relation to proximal end 18 of cannula 12. Mounting member 54 may be permanently secured to proximal end 18 of retractor 12, or may be removably secured to proximal end 18 to facilitate insertion of retractor 12. In one embodiment, mounting member 54 includes a ring shaped configuration that extends completely around retractor 12 to provide a stable mounting of guide member 40 to retractor 12. The ring shaped mounting member 54 defines a passage that forms a proximal extension of the passage defined by retractor 12.

Instrument 80 includes an elongated shaft 82 extending along a longitudinal axis 84 between a distal end 86 and an opposite proximal end 88. Distal end 86 is configured to engage in a recess 102 of bone anchor 100. Shaft 82 includes a length configured to extend from distal end 16 of retractor 12 through guide member 40. In addition, shaft 82 includes an outer dimension configured to extend through slot 52. Apparatus 10 also includes a clamping mechanism 90 adjacent to proximal end 88. As further shown in FIG. 3, clamping mechanism 90 includes a first sleeve member 92 through which shaft 82 extends. A clamping member 94 extends around and is engaged to sleeve member 92. Clamping member 94 and sleeve member 92 have a first, unlocked position in which distal end 94a of clamping member 94 is spaced from proximal side 50 and flange 92a of sleeve member 92 is spaced from distal side 48 of body portion 42 of guide member 40. In the unlocked position of FIG. 3, instrument 80 is movable along slot 52 to change its trajectory into the patient and relative to retractor 12.

Figure 1:
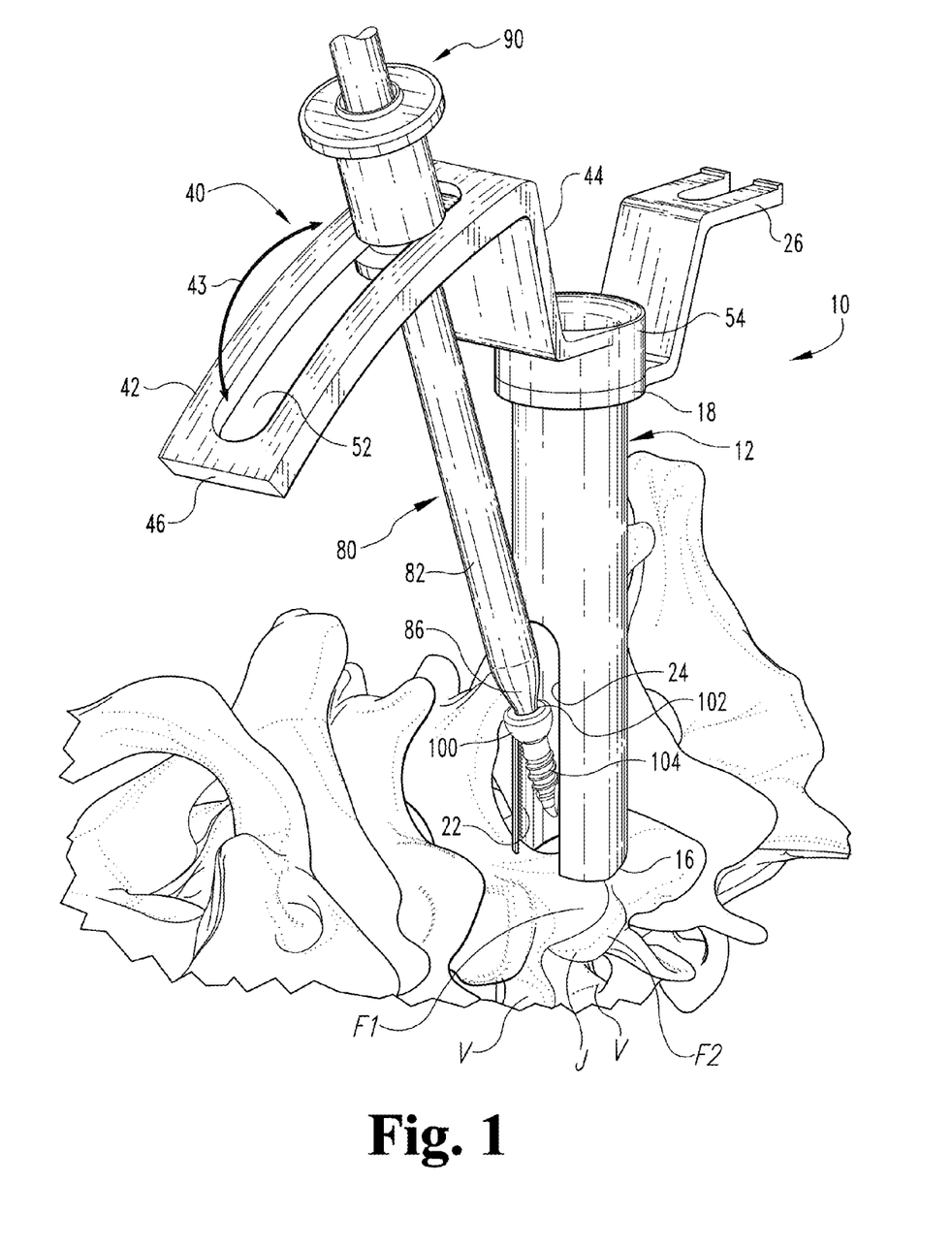
FIG. 1 is a perspective view of a spinal column segment and a surgical apparatus for minimally invasive insertion of a bone anchor for facet fixation.
Figures 2, 3:
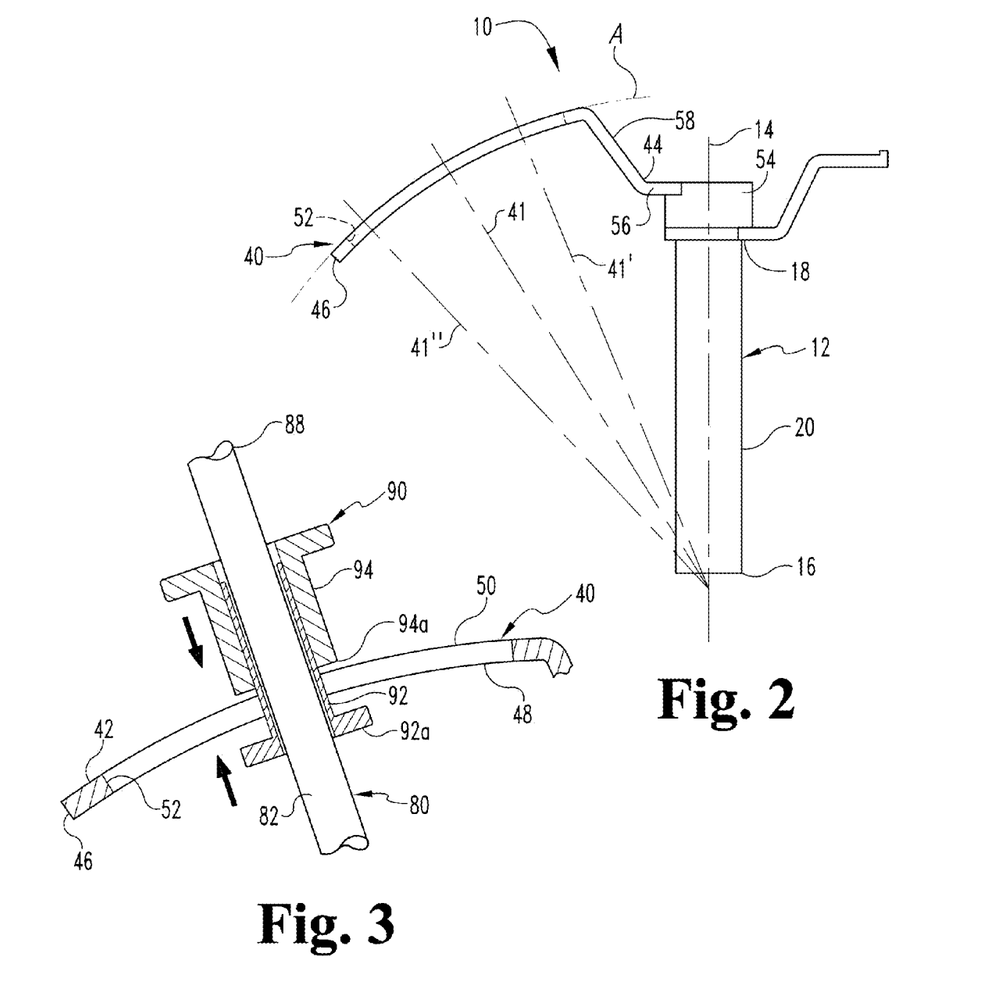
FIG. 2 is an elevation view of the apparatus of FIG. 1.
FIG. 3 is a section view of a portion of the apparatus of FIG. 1.
Figure 4:
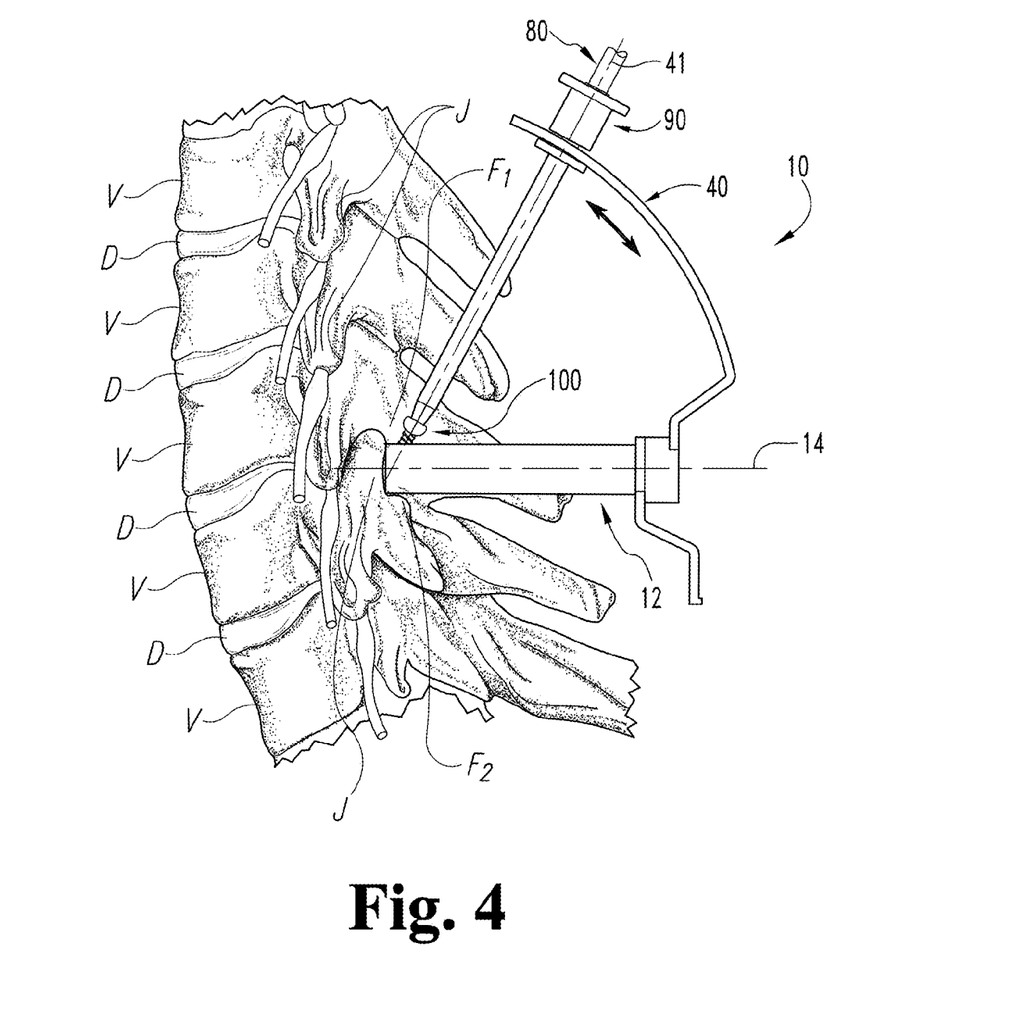
FIG. 4 is a side elevation view of a portion of the spinal column segment showing the surgical apparatus guiding a bone anchor for engagement to the facet joint.

Clamping mechanism 90 includes a second, locked position as shown in FIGS. 1 and 4, in which distal end 94a and flange 92a contact the respective adjacent side of body portion 42 of guide member 40 to lock instrument 80 in position and trajectory along slot 52 while simultaneously allowing instrument 80 to be translated and/or rotated along the selected trajectory. In the second position, clamping member 94 draws sleeve member 92 toward guide member 40 until distal end 94a of clamping member 94 contacts proximal side 50 of body portion 42 and flange 92a of sleeve member 92 contacts distal side 48 of body portion 42 of guide member 40. Clamping mechanism 90 can be readily unlocked to move instrument 80 along guide member 40 to another trajectory and then quickly locked to secure instrument 80 in the revised trajectory. In one embodiment, clamping member 94 is threadingly engaged about sleeve member 92 to move clamping mechanism 90 between the locked and unlocked positions. Other embodiments contemplate other arrangements to secure members 92, 94 to one another, including bayonet locks, friction locks and other suitable engagement relationships.

Various configurations for retractor 12 are contemplated. In the illustrated embodiment, retractor 12 includes an elongated tubular body 20 defining a passage in the form of a working channel 22 that extends between and opens at distal end 16 and proximal end 18. Body 20 includes a circular cross-section orthogonal to longitudinal axis 14. Other embodiments contemplate non-circular cross-sections, including oval, hemi-oval, racetrack, elliptical, polygonal, and irregular cross-sections, for example. Body 20 includes a length between distal and proximal ends 16, 18 sized to extend from a working site at or near the bony structure of the patient to or through the skin level of the patient. Working channel 22 is sized to allow one or more instruments to be positioned therethrough to perform procedures at the working space adjacent to distal end 16. Proximal end 18 of retractor 12 includes a mounting bracket 26 extending laterally therefrom. Mounting bracket 26 can be mounted to a flexible arm or other structure that is secured to the operating table or other base to provide stability to retractor 12 when positioned in the patient.

Body 20 also includes a window 24 extending from distal end 16 in a proximal direction. Window 24 provide a path or avenue into working channel 22 from a location outside body 20. In the illustrated embodiment, body 20 does not completely enclose window 24 and window 24 is open at distal end 16. In other embodiments, window 24 may be enclosed on all of its sides by body 20. Window 24 is elongated along longitudinal axis 14 to accommodate placement of instrument 80 and anchor 100 at various trajectories therethrough. The relatively large working channel 22 is configured to allow direct visualization of anchor 100 and instrument 80 at the working space adjacent to distal end 16 of retractor 12. Direct visualization can be conducted by naked eye visualization or loupes. In one embodiment, working channel 22 includes a diameter of more than 10 millimeters. In addition, working channel 22 can receive an endoscope or other viewing instrument to facilitate viewing of the working space.

In the illustrated embodiment, working channel 22 forms a passage that is completely enclosed by body 20. Other embodiments contemplate that the passage is partially enclosed by the body of retractor 12. In any event, the passage lies on or extends along longitudinal axis 14 so that an anchor 100 guided along any trajectory 41 defined by guide member 40 is advanced to a location referenced to retractor 12. In the illustrated embodiment, body portion 42 of guide member 40 and slot 52 extend along an are and define an infinite number of trajectories 41 between and including maximum and minimum trajectories 41', 41" located at the opposite ends of slot 52. Each of the trajectories 41 extends in an orthogonal orientation to the tangent of the arc at the location where the respective trajectory 41 intersects the arc. Each of trajectories 41 intersects retractor 12 or an extension of retractor 12 so that the anchor 100 guided with instrument 80 will extend through window 24 and into the bony structure at distal end 16 of retractor 12, allowing direct visualization of anchor placement through working channel 22. Other embodiments contemplate arrangements where one or more the trajectories intersects or is offset from longitudinal axis 14.

FIGS. 1 and 4 show apparatus 10 in position relative to a portion of a spinal column segment including a facet joint. The spinal column segment includes a number of vertebrae V, with adjacent one of vertebrae V separated by a respective one of spinal discs D. Facet joints J are located between respective ones of adjacent vertebrae V. Facet joints J each include a superior facet F1 and an inferior facet F2. It is contemplated that the spinal column segment is part of a patient in which spinal surgery is to be performed with the present invention. It is also contemplated that the spinal column segment may comprise a non-human or non-living animal substrate, such as may be present with a training model to teach methods employing the surgical instruments and implants discussed herein.

Retractor 12 is positioned through a minimally invasive portal to the target facet joint J. The skin and/or tissue may be dilated sequentially, by a balloon, or by any suitable means prior to placement of retractor 12. Once retractor 12 is aligned over the target facet joint J, guide member 14 can be attached if not pre-attached to retractor 12. The alignment of retractor 12 positions guide member 40 so that the trajectories 41 defined thereby are oblique to retractor 12 and axis 14 and so that at least one of the trajectories 41 intersects facet joint J so that anchor 100 can extend through facets F1, F2. Anchor 100 is engaged through facets F1, F2 with instrument 80 along a selected trajectory 41 defined by body portion 42 of guide member 40. Bone anchor 100 is guided and driven into bone by instrument 80 in one embodiment. In the illustrated embodiment, anchor 100 is a bone screw and includes a bone engaging portion 104 that extends through superior facet F1 and into inferior facet F2 to fix the facet joint. Other embodiments contemplate other configurations for bone engaging portion 104 and/or anchor 100, including partially threaded shafts, non-threaded shafts, and expandable shafts, for example.

In FIGS. 1 and 4, for the sake of clarity, the skin and surrounding tissue of the patient's body is not depicted. It should be appreciated that retractor 12 can be inserted to facet joint J through a first minimally invasive insertion path through the skin and tissue that is sized to accommodate retractor 12 but not other portions of apparatus 10. Guide member 40 extends laterally from a proximal end of retractor 12 in a cephalad direction and is located above or proximal to the skin level of the patient. Instrument 80 extends from guide member 40 and through the skin and tissue along a separate, second minimally invasive insertion path through the skin and tissue that is formed by or defined by instrument 80. In one embodiment, instrument 80 and anchor 100 are cannulated and guided to superior facet F1 along a guide wire or dilator to the target location. During or prior to anchor insertion, a hole can be formed in facet F1 and/or F2, or other bone preparation can be completed, using guide 40 and a suitable instrument 80 along trajectory 41.

Prior to insertion of anchor 100, the facet joint J can be prepared by removing, scraping, forming, drilling, reaming, or tapping bone material to facilitate insertion of anchor 100. Although the apparatus 10 is shown in FIGS. 1 and 4 as being inserted via an incision lateral to the spinous process SP (e.g., an ipsilateral incision or a contralateral incision), insertion via a midline, lateral or oblique approach or orientation is also contemplated. The retractor 12 and bone anchor 100 can be inserted percutaneously through separate incisions. For example, in some embodiments, the retractor 12 and bone anchor 100 can each be inserted in a minimally-invasive manner through separate incisions that each has a size less than 15 mm.

In some embodiments, the method optionally includes coupling the bone anchor 100 to the distal end of an instrument 80 that is a driver while bone anchor 100 is outside the patient. The driver instrument 80 is inserted through or along guide member 40 and into the patient with bone anchor 100 attached thereto. In some embodiments, instrument 80 includes a sleeve around the driver to facilitate placement of the anchor into the patient. In other embodiments, for example, the bone anchor 100 can be removably coupled to the distal end portion of the driver instrument by a friction fit, clamp, retention member, a snap ring, a magnetic coupling, an adhesive coupling or the like. Instrument 80 can be inserted under fluoroscopic guidance or other suitable viewing system. A passageway is defined within the tissue while instrument 80 is disposed within the patient's body. In some embodiments, the passageway can be defined using a sleeve or retractor extending from guide member 40. In other embodiments, the passageway is defined by a separate retractor, tube, sleeve or other device to accommodate instrument 80 and/or anchor 100.

Although various embodiments have been described as having particular features and/or combinations of components, other embodiments are possible having a combination of any features and/or components from any of embodiments as discussed above. As used in this specification, the singular forms "a," "an" and "the" include plural referents unless the context clearly dictates otherwise. Thus, for example, the term "a member" is intended to mean a single member or a combination of members, "a material" is intended to mean one or more materials, or a combination thereof. Furthermore, the terms "proximal" and "distal" refer to the direction closer to and away from, respectively, an operator (e.g., surgeon, physician, nurse, technician, etc.) who would insert the medical implant and/or instruments into the patient. For example, the portion of a medical instrument first inserted inside the patient's body would be the distal portion, while the opposite portion of the medical device (e.g., the portion of the medical device closest to the operator) would be the proximal portion.

While the application has been illustrated and described in detail in the drawings and foregoing description, the same is to be considered as illustrative and not restrictive in character, it being understood that only the selected embodiments have been shown and described and that all changes, modifications and equivalents that come within the spirit of the invention as defined herein or by any of the following claims are desired to be protected.

What is claimed is:

1. An apparatus, comprising:
   a retractor including an elongated body extending along a longitudinal axis between a distal end and an opposite proximal end, said retractor defining a passage between said distal and proximal ends, said retractor further including a window through said body opening into said passage adjacent to said distal end, said retractor being configured for positioning in a body of a patient with said distal end adjacent an implantation location in the body of the patient while said proximal end is located outside the body of the patient;
   a guide member extending laterally from said proximal end of said retractor, said guide member including an elongated body portion extending along an arc, said arc of said body defining a plurality of trajectories relative to said longitudinal axis of said retractor and each of said plurality of trajectories further intersects said window of said retractor; and
   an instrument removably mounted to said guide member, said instrument being movable along said guide member and securable to said guide member in any selected one of said number of trajectories so that said instrument can be moved along a selected one of said trajectories through said window, said instrument including a elongated shaft extending through a slot of said guide member and a clamping mechanism, said elongated shaft being slidably disposed within a passageway of a sleeve member of said clamping mechanism, said sleeve member being slidably disposed within a passageway of a clamping member of said clamping mechanism, said clamping member and said sleeve member being configured to move relative to one another engage opposite surfaces of said guide member to releasably secure said instrument in said selected trajectory through said window.

2. The apparatus of claim 1, wherein each of said plurality of trajectories intersects said arc at a respective one of a plurality of tangents to said arc with each of said trajectories extending in an orthogonal relationship to said respective tangent.

3. The apparatus of claim 1, wherein said retractor includes a tubular body and said passage defines a working channel extending between said distal end and said proximal end, said passage comprising openings at said distal and proximal ends that coaxial with said longitudinal axis.

4. The apparatus of claim 3, wherein said window opens at a side of said tubular body of said retractor, said window further extending through a distal end surface of said tubular body and opening at said distal end of said tubular body.

5. The apparatus of claim 1, wherein said clamping member is monolithic.

6. The apparatus of claim 1, wherein said guide member includes an inner end portion mounted to said proximal end of said retractor and said body portion of said guide member extends from said inner end portion to an opposite outer end.

7. The apparatus of claim 6, wherein said inner end portion of said guide member is removably mounted to said proximal end of said retractor.

8. The apparatus of claim 7, wherein said retractor includes a tubular body and said inner end portion includes a ring-shaped mounting member positioned on said proximal end of said tubular body of said retractor.

9. The apparatus of claim 8, wherein said inner end portion includes a first arm portion extending laterally from said mounting member and a second arm portion extending proximally and obliquely from said first arm portion to said body portion of said guide member, said body portion of said guide member extending laterally from said second arm portion to said outer end of said body portion.

10. The apparatus of claim 1, wherein said instrument is rotatable and translatable along said selected trajectory relative to said guide member when said instrument is releasably secured in said selected trajectory.

11. The apparatus of claim 1, wherein said trajectories each define a different angle relative to said longitudinal axis, said elongated body portion being continuously curved along said arc, said instruments being movable along said arc to move said instrument between said trajectories.

12. The apparatus of claim 1, wherein
   said opposite surfaces are inferior and superior surfaces of said guide member, said slot extending through said inferior and superior surfaces; and
   a first planar face of said sleeve member engages said inferior surface and a second planar face of said clamping member engages said superior surface to releasably secure said instrument in said selected trajectory.

13. The apparatus of claim 12, wherein said sleeve member comprises a flange that extends outwardly from a body of said sleeve member and includes said first planar face and an opposite third planar face, said clamping member comprising a second flange opposite said second planar face that extends outwardly from a body of said clamping member, said flanges being configured to be moved toward one another to releasably secure said instrument in said selected trajectory.

14. The apparatus of claim 1, wherein said guide member includes a ring-shaped mounting member permanently secured to said proximal end of said refractor, said body portion of said guide member extending from said mounting member in a first direction, said mounting member comprising a bracket extending therefrom in an opposite second direction, said bracket comprising a slot configured to engage a surgical device.

15. The apparatus of claim 14, wherein said mounting member comprises a through hole that is in communication with said passage such that a surgical instrument can be passed through said through hole and into said passage.

16. The apparatus of claim 1, further comprising a bone anchor including a threaded shaft connected to a head comprising a socket, wherein a distal tip of said elongated shaft is disposed in said socket such that rotation of said instrument rotated said bone anchor.

17. The apparatus of claim 1, wherein said sleeve member has a first portion slidably disposed within said passageway of said clamping member and a second portion slidably disposed within said slot.

18. An apparatus, comprising:
  a retractor including an elongated tubular body extending along a longitudinal axis between a distal end and an opposite proximal end, said tubular body defining a working channel between said distal and proximal ends, said retractor further including a window opening through said tubular body into said working channel, said window extending proximally from said distal end of said tubular body, said retractor being configured for positioning in a body of a patient with said distal end adjacent an implantation location in the body of the patient while said proximal end is located outside the body of the patient;
  a guide member extending laterally from said proximal end of said retractor, said guide member including an elongated body portion defining a plurality of trajectories that each intersect said window of said retractor,
  a driver instrument removably mounted to said body portion of said guide member, said driver instrument being movable along said body portion of said guide member, said driver instrument including an elongated shaft extending through a slot of said guide member and a clamping mechanism, said elongated shaft being slidably disposed in a passageway of a sleeve member of said clamping mechanism, said sleeve member being slidably disposed within a passageway of a clamping member of said clamping mechanism, said clamping member and said sleeve member being configured to move relative to one another to engage opposite surfaces of said guide member to releasable secure said instrument in a selected one of said trajectories through said window; and
  a bone anchor removably engaged to a distal end of said driver instrument, said bone anchor being positioned through said window along said selected trajectory for implantation into bony structure under direct vision through said working channel of said retractor.

19. The apparatus of claim 18, wherein said bone anchor is a bone screw comprising a threaded shaft connected to a head comprising a socket, said socket having a distal end of said driver instrument removable disposed therein such that a rotation of said driver instrument rotates said bone anchor.

20. The apparatus of claim 18, wherein said body portion of said guide member extends along an arc, said body portion defining said plurality of trajectories where each of said plurality of trajectories intersects said body portion at a respective tangent of said arc of said body portion with each of said trajectories in an orthogonal relationship to said respective tangent.

* * * * *

UNITED STATES PATENT AND TRADEMARK OFFICE
CERTIFICATE OF CORRECTION

Page 1 of 2

PATENT NO. : 9,474,538 B2
APPLICATION NO. : 13/552378
DATED : October 25, 2016
INVENTOR(S) : Foley et al.

It is certified that error appears in the above-identified patent and that said Letters Patent is hereby corrected as shown below:

In the Specification

In Column 4, Line 11, delete "guide member portion 42" and insert -- guide member portion 40 --, therefor.

In Column 5, Line 54, delete "an are and" and insert -- an arc and --, therefor.

In Column 6, Line 20, delete "guide member 14" and insert -- guide member 40 --, therefor.

In the Claims

In Column 8, Line 7, in Claim 1, delete "including a elongated" and insert -- including an elongated --, therefor.

In Column 8, Line 15, in Claim 1, delete "another engage" and insert -- another to engage --, therefor.

In Column 8, Line 28, in Claim 3, delete "that coaxial" and insert -- that are coaxial --, therefor.

In Column 8, Line 62, in Claim 12, delete "wherein" and insert -- wherein: --, therefor.

In Column 9, Lines 1-2, in Claim 12, delete "releaseably" and insert -- releasably --, therefor.

In Column 9, Line 14, in Claim 14, delete "refractor," and insert -- retractor, --, therefor.

In Column 9, Line 23, in Claim 15, delete "through said through hole" and insert -- through said hole --, therefor.

In Column 9, Line 28, in Claim 16, delete "rotated" and insert -- rotates --, therefor.

Signed and Sealed this
Fourteenth Day of February, 2017

Michelle K. Lee
*Director of the United States Patent and Trademark Office*

CERTIFICATE OF CORRECTION (continued)
U.S. Pat. No. 9,474,538 B2

In Column 10, Line 21, in Claim 18, delete "releasable" and insert -- releasably --, therefor.

In Column 10, Line 32, in Claim 19, delete "removable" and insert -- removably --, therefor.

In Column 10, Line 33, in Claim 19, delete "a rotation" and insert -- rotation --, therefor.